United States Patent [19]
Gabeler et al.

[11] Patent Number: 5,423,661
[45] Date of Patent: Jun. 13, 1995

[54] FLUID METERING, MIXING AND COMPOSITION CONTROL SYSTEM

[75] Inventors: Stephen C. Gabeler, Sudbury; William W. Carson, Hopkinton, both of Mass.

[73] Assignee: Millipore Corporation, Bedford, Mass.

[21] Appl. No.: 235,007

[22] Filed: Apr. 28, 1994

Related U.S. Application Data

[62] Division of Ser. No. 929,051, Aug. 13, 1992, abandoned.

[51] Int. Cl.⁶ .................. B01D 15/08; F04B 17/00
[52] U.S. Cl. .................. 417/410.4; 417/420; 418/188; 210/101; 210/198.2
[58] Field of Search .......... 210/635, 656, 659, 198.2, 210/101, 258, 416.1, 541; 417/410.3, 410.4, 420; 418/188

[56] References Cited

U.S. PATENT DOCUMENTS

| | | | |
|---|---|---|---|
| 1,076,299 | 10/1913 | Marshall | 418/188 |
| 1,418,741 | 6/1922 | Stallman | 418/188 |
| 1,843,246 | 2/1932 | Sloane | 418/188 |
| 2,400,485 | 5/1946 | Cardillo | 418/188 |
| 2,737,341 | 3/1956 | Bitzer | 418/188 |
| 3,238,883 | 3/1966 | Martin | 417/420 |
| 3,259,073 | 7/1966 | Burtis | 418/188 |
| 3,716,306 | 2/1973 | Martin | 417/420 |
| 3,975,946 | 8/1976 | Ball | 73/61.1 C |
| 3,986,797 | 10/1976 | Kopf | 417/420 |
| 4,036,062 | 7/1977 | Cruzan | 73/422 GC |
| 4,065,235 | 12/1977 | Furlong | 417/420 |
| 4,111,614 | 9/1978 | Martin | 417/420 |
| 4,127,365 | 11/1978 | Martin | 417/420 |
| 4,165,206 | 8/1979 | Martin | 417/420 |
| 4,583,924 | 4/1986 | Zenglein | 417/420 |
| 4,595,496 | 6/1986 | Carson | 210/198.2 |
| 4,840,730 | 6/1989 | Saxena | 210/659 |
| 4,846,641 | 7/1989 | Pieters | 417/420 |
| 4,895,806 | 1/1990 | Le | 435/288 |
| 5,158,704 | 10/1992 | Fulton | 210/656 |

OTHER PUBLICATIONS

Snyder, Introduction to Modern Liquid Chromatography, John Wiley & Sons, New York, 1979, pp. 90–103.

*Primary Examiner*—Ernest G. Therkorn

[57] ABSTRACT

A gear pump is used for the primary flow source for a low pressure, high performance separation system. The pump is controlled such that its flow and leakage characteristics are compensated by an electronic controller which results in controlled output flow rates to a variety of loads. The pump is particularly suited for use in liquid chromatography (LC) systems, especially LC systems which use membrane based separation media. A modification to the gear pump results in an efficient mixer, further enhancing its use in LC systems which involve gradient operational modes. Also disclosed are embodiments which allow the gear pump to be used in high pressure separation systems, e.g., high performance liquid chromatography (HPLC) systems.

2 Claims, 11 Drawing Sheets

FLUID METERING, MIXING AND COMPOSITION CONTROL SYSTEM

This is a division of application Ser. No. 07/929,051 filed on Aug. 13, 1992, now abandoned.

FIELD OF THE INVENTION

This application relates generally to the pumping, mixing and metering of liquids in controlled proportions especially as utilized in both high and low pressure liquid chromatography (LC) systems. The invention pertains to the ability to control the proportions of mixed liquids smoothly and precisely over a given total volume of the liquid delivered with small delay volumes when the proportions are changed.

BACKGROUND OF THE INVENTION

U.S. Pat. No. 4,595,496 to William W. Carson (Carson) gives a good summary of liquid chromatography (LC), which is one important application of the present invention. The entire disclosure of said patent is hereby incorporated by reference into this application as though set in full herein.

In LC, a liquid sample is placed (injected) into a flowing stream of a liquid carrier (mobile phase), that flows through a separation device such as a packed column or membrane (stationary phase). While passing through the separation device, the various components of the sample are adsorbed and desorbed from the stationary phase at different rates thereby separating the components into different volumes (and times) eluting from the separation device. The various components then flow through a detector (or several detectors) that respond to the components, thereby providing qualitative and quantitative data about the components.

LC systems, to separate more effectively, often use fixed composition mixtures of fluids as the mobile phase (isocratic mode), and, in addition, often change the mixture composition over a total volume (or time) delivered (gradient mode) to achieve a more effective separation of the sample components.

LC systems, at least, provide for one or several fluids as mobile phases, valves to select and inject each of the fluids, a pump to deliver (delivery pump) the fluid(s) at a given flow rate, and a column of packed particles or a membrane stationary phase to separate the sample components. Often a means to detect the separated sample components is also included. In addition mixers, accumulators and other flow elements are used in specific applications.

In high pressure applications, LC systems commonly use high cost, gear driven piston pumps with high pressure sliding seals at the interface between the drive member (piston) and the housing containing the drive (cylinder). While the seals may either be fixed in position on the walls of the cylinder or disposed on the piston itself, hereinafter, "sliding seals" refers generically to those seals which separate the driven LC fluids from the outside environment, e.g., the air, regardless of how configured. Typically elements of the system are alternately wetted with the LC fluids and then with the outside environment as they pass over the seals. There will be some small amount of leakage past these seals, and if the leakage produces a residue, for example a salt from a dried buffer solution, that residue can cause wear of the seal which leads to a system failure. This occurrence is a major limitation and one of the primary failure modes or maintenance issues of such pumps.

Another limitation of LC piston pumping systems is that the alternate exposure to the fluid path and then to the outside environment provides an opportunity for extraneous substances to enter the fluid path and the LC system thus adulterating the analysis. In this manner LC system applications using sterile fluids may become non-sterile. This is of particular interest when biologically active compounds are being separated. Them is a need in such systems to eliminate this source of contamination.

Piston pumps with either single or multiple pistons also produce flow fluctuations which correspond to the reciprocating cycle of the piston(s). These fluctuations result from variations in piston velocity through the stroke and from the check valves typically used to switch the source of flow from one piston to another.

For low pressure applications, LC fluids are driven in a variety of ways, including simple gravity feed and the use of external gas pressure supplied to the fluid reservoirs. Another common low pressure drive involves the use of peristaltic pumps in which one or more rollers impinge on a tube containing the LC fluid thereby propelling the fluid through the system. Such pumps also produce flow fluctuations corresponding to the roller impingement on the fluid delivery tube. In addition, the tubes are elastic, can lose their shape or even wear out, further producing inaccurate delivery of called-for flow. Thus there is a need in these applications for longer lived mechanisms that deliver more constant fluid flows. There is also a continuing need to reduce or eliminate sliding seal leakage and to produce low cost pumps with reduced fluctuation effects.

In fluid pumping systems, especially high pressure LC systems, fluid metering is important. Such high pressure LC systems using commercially available columns generally require precise flow rates. If the flow rate varies due to hydrostatic loading, e.g. as a column fluid flow resistance changes, or as other detectors are used, the separation may be affected. Flow metering herein is defined as providing precise and repeatable flow rates. Accurate flow rates are not easily achieved for many reasons, e.g., compressibility of the fluids, non-linear mixing of the fluids, temperature dependencies. Piston pumps provide precise flow rates based on the precise machining of piston/cylinders and controlled actuation of the pumps. In order to repeat and/or verify analyses, the volume (or time) in which a sample component elutes from a column must be reproducible, so the flow rate must be reproducible. The fundamental basis of separation will determine the degree of flow accuracy which is required for reproducibility.

Both high and low pressure LC pumps generally have fluctuations in delivered flow rate, corresponding to the fundamental and harmonic frequencies of the pump driving mechanism, with periods ranging from tens of milliseconds to many seconds. This is particularly troublesome in gradient systems as flow fluctuations can result in composition fluctuations. In a gradient application, the gradient may be formed by proportioning valves on the intake side of the pump, each valve leading to a different fluid component or mixture. This is commonly referred to as low pressure gradient formation. In one configuration the proportioning valves, operating as taught by Carson, provide the desired gradient fluid compositions while minimizing the effects of flow fluctuations in the pump. In such a gradient formation system, some form of mixer is required in order to filter out residual high frequency composition fluctuations. Under-filtering (mixing) allows residual fluctuations to remain in the system. Over-filtering limits the speed of composition response of the system and complex mixers add cost.

There is a need for smoother, quicker responding gradient pumping systems, and it is advantageous to eliminate extra flow elements, like separate mixers, wherever possible.

In addition, there have been advances in membrane separation media for LC applications. U.S. Pat. No. 4,895,806, to Minh Son Le and James Alan Sanderson describes such an advancement, and the entire disclosure of said patent is hereby incorporated by reference into this application as though set in full herein. Compared to many LC separation devices, such membrane devices operate at high flow rates; lower pressures, and with separations which depend more upon fluid compositions than highly precise flow rates. These devices have also been shown to be of particular utility in the separation of biologically active compounds.

There is an opportunity for a pumping system where the pump matches the needs of such membrane separation devices. These needs include smooth precise control, rapid composition response and the elimination of composition fluctuations.

Gear pumps have been used in LC systems as a priming and/or pre-pump working with the primary system pump. In such uses, the gear pump is not the primary flow source, instead it provides an assist to maintain priming of the primary delivery pump. A typical gear pump is shown in U.S. Pat. No. 4,111,614 to Thomas B. Martin et al. The pumping characteristics and construction details of this type of pump are well known in the art. The construction of a gear pump has a leakage path from the output back to the input such that a positive pressure differential between the output and the input will force fluid to flow in opposition to the primary flow of the pump. Thus, for a given pump rotation rate, if there is a change in hydraulic resistance of the load, the resulting flow through the load will change and the difference will flow through the leakage path. If this occurs, the timing of the chromatographic separation may change necessitating continued experimentation. Commercially available gear pumps are typically limited to pressures of a few hundred pounds per square inch. Many chromatography systems require higher pressures and more easily controlled flow rates from primary delivery pumps. In addition, the construction of these lower cost gears pumps leads to performance differences from pump to pump, especially the hydraulic resistance of the output to input leakage path, which make it difficult to control the flow in a load or separation device. These preceding limitations have likely contributed to the non-use of a gear pump as the primary LC delivery pump.

However, gear pumps have advantages such as being low cost and capable of high flow rates; in addition, they may be magnetically coupled with no sliding seals thus overcoming some of the above limitations of piston pumps.

It is an object of this invention to provide a fluid gradient and fluid composition mixing system with a small delay volume.

It is another object of this invention to provide a pumping system with reduced flow fluctuation, smoother and faster gradient response. It is another object of this invention to provide such a system at a low cost.

It is another object of this invention to provide an LC system appropriate to the specific requirements of membrane based separation devices.

It is yet another object of this invention to provide pump metering systems useful at both high and low system pressures.

It is a further object of this invention to provide a pumping system which eliminates cross contamination between the pumped fluid and the external environment.

It is another object of this invention to provide an LC system with improved pump reliability.

SUMMARY OF THE INVENTION

The foregoing objects are met in a system utilizing a gear pump, or equivalent thereof, as the primary system pump. A control system is provided to compensate for the flow and the leakage characteristics of the gear pump, whereby the pump will deliver a controlled flow to a variety of loads. In a preferred embodiment, a pressure transducer immediately downstream from the pump and a tachometer on the drive motor for the gear pump are used in a controlled feed back arrangement via an electronic system controller (any microprocessor or other computer may be used to advantage) to produce the controlled flow rate. The present invention will have advantage for any liquid pump wherein the flow rate is controllable, and will have particular advantage for such pumps in LC applications using membrane separation media.

A preferred system comprises a mixer inherent within a gear pump that provides a mixing volume around the magnetic pump rotor adjacent to the gears.

In another embodiment of the system the gear pump and an associated controller are constructed and operated so that the pressure across the gear pump is substantially zero. In this manner the gear pump provides a controlled flow rate, and it is utilized as a metering pump in a high pressure LC system configured such that the high pressure is common mode pressure to the gear pump. That is, the high pressure appears at both the inlet and outlet of the gear pump with substantially zero pressure across the gear pump.

In yet another preferred embodiment, the gear pump is similarly constructed; however, this combination is configured such that the output of the gear pump operates near atmospheric pressure and an in-line second pump is used to boost the pressure to the higher system operating pressure. This second pump may be servo controlled to maintain the metering gear pump outlet pressure at substantially the same pressure as its inlet pressure, or it may be a pump which will accept varying flow rates while holding inlet pressure constant. It is also possible, in this preferred embodiment, to pressurize the system such that the gear pump outlet pressure is elevated above atmospheric pressure.

In yet another embodiment a magnetically coupled gear pump provides for no sliding seals which eliminates leakage of fluid from the pump to the external environment, and also eliminates a source of contamination.

The present invention is used to advantage with a compositional gradient valve apparatus, such as disclosed by Carson. Carson recognized that pump cycle periods and switching valve periods must be controlled to minimize fluctuations in composition. In addition this patent recognized that inertia of the flowing liquid will lead to inaccuracies at some flow rates when combined with short valve duration times.

Other objects, features and advantages will be apparent from the following detailed description of preferred embodiments thereof taken in conjunction with the accompanying drawings.

DETAILED DESCRIPTION OF PREFERRED EMBODIMENTS

Figure 1:
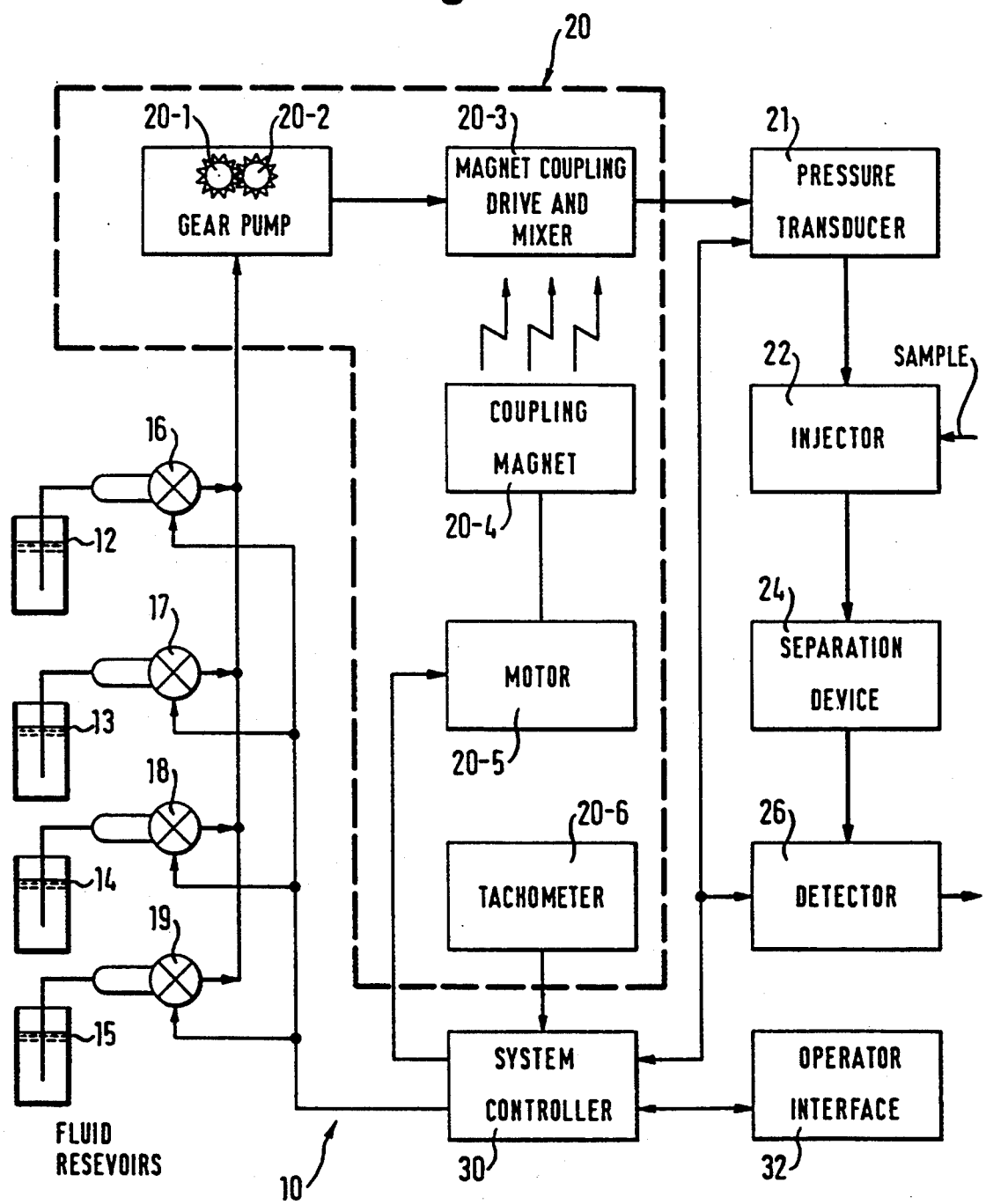
FIG. 1 is a schematic block diagram of an LC system, with liquid delivery means, according to a preferred embodiment of the invention.

FIG. 1 shows a liquid chromatography (LC) system 10 having four fluid reservoirs 12, 13, 14 and 15 that are plumbed into a gear pump 20 through four valves 16, 17, 18 and 19. A system controller 30, responsive to inputs previously loaded and currently measured, controls the flow rate by driving the gear pump and controls the mixture of fluids by driving the valves 16, 17, 18 and 19. The gear pump is shown as including pumping gears 20-1 and 20-2, a magnetic coupling drive and mixer 20-3, a coupling magnet 20-4 external to the fluid flow path, a motor 20-5, and a tachometer 20-6. A pressure transducer 21, which may be of any compatible type known in the art, is positioned just downstream from the pump. The system is completed by injector 22, separation device 24, and detector 26, all of which may be of any compatible type known in the art. The operator interface 32 consists of a keyboard and display (not shown) connected to the system controller and provides for operator programming of flow rates and composition gradients and operator participation in various calibration procedures.

In operation, the gear pump 20 draws fluid from the reservoirs 12, 13, 14 and 15 via the proportioning valves 16, 17, 18 and 19 which, are operated to provide a desired mixture of fluids under the control of the system controller 30. The fluid mixture is pumped by gears 20-1, 20-2 through the mixer 20-3. The pressure of the fluid mixture is measured by transducer 21 and the pump speed is measured by tachometer 20-6. The system controller, using the inputs of pressure and pump speed and other stored prior inputs, drives the gear pump to provide a controlled fluid flow rate.

Continuing with the system operation, a sample is injected into the flowing stream at injector 22, and a separation device 24 separates the components of the sample. The separated components are detected by detector 26. The detector signal is delivered to an appropriate external apparatus (not shown) for display and/or further processing. The stream containing the separated components is delivered to an external collecting apparatus (not shown).

Figure 2A:
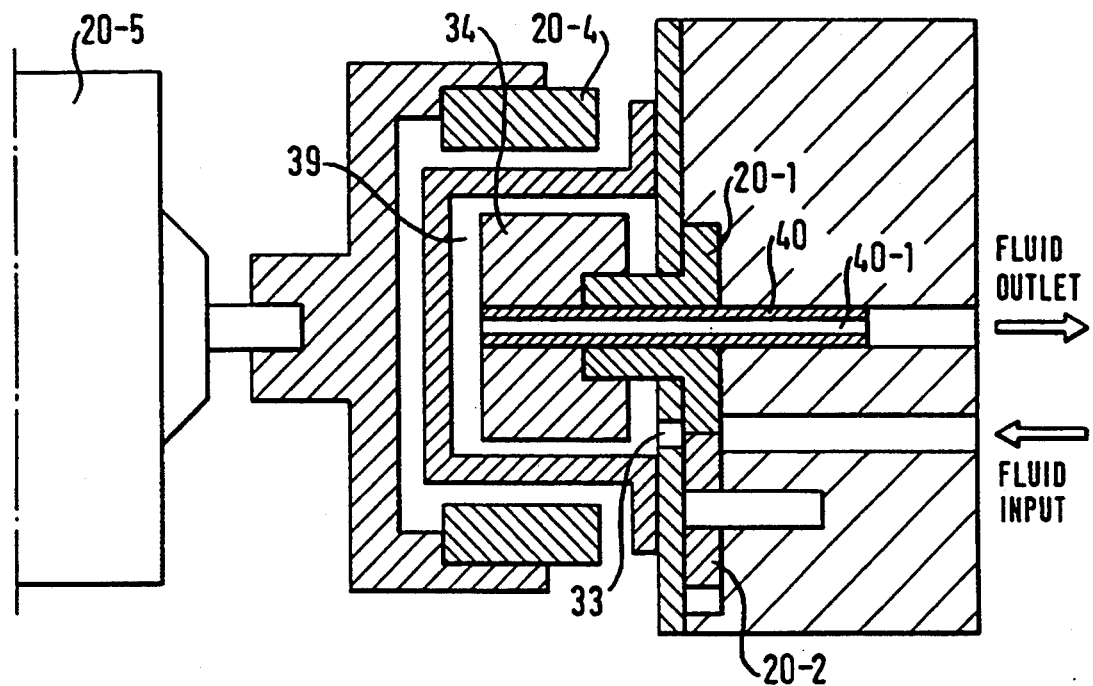
FIGS. 2A and 2B are sectioned drawings of a gear pump usable in the preferred embodiments.
Figure 2B:
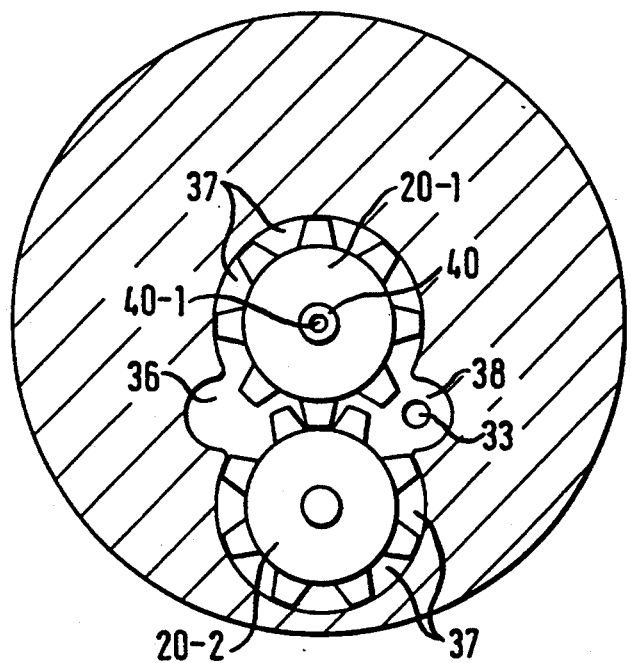

FIGS. 2A and 2B show the gear pump 20 in more detail. In FIG. 2B fluid enters into chamber 36 and is carried in the volumes formed by the spaces 37 between the gear teeth and the enclosing walls from chamber 36 to chamber 38 by the rotation of the gears. A tight fit between the gear teeth and the walls, the gear faces and the enclosure, and the mesh point of the gears inhibits the fluid from flowing back from chamber 38 to chamber 36. In many conventional gear pumps there is an outlet from the pump directly from chamber 38, but in this preferred embodiment the fluid path is from chamber 38 through port 33, into the cylindrical chamber 39 (see FIG. 2A) formed around the drive magnet 34, and out through a hollow core 40-1 in bearing shaft 40 on which the drive magnet and drive gear ride. Other details of construction of the gear pump, such as the lack of sliding seals between the fluid path and the external environment, are as practiced in the art.

Figure 3:
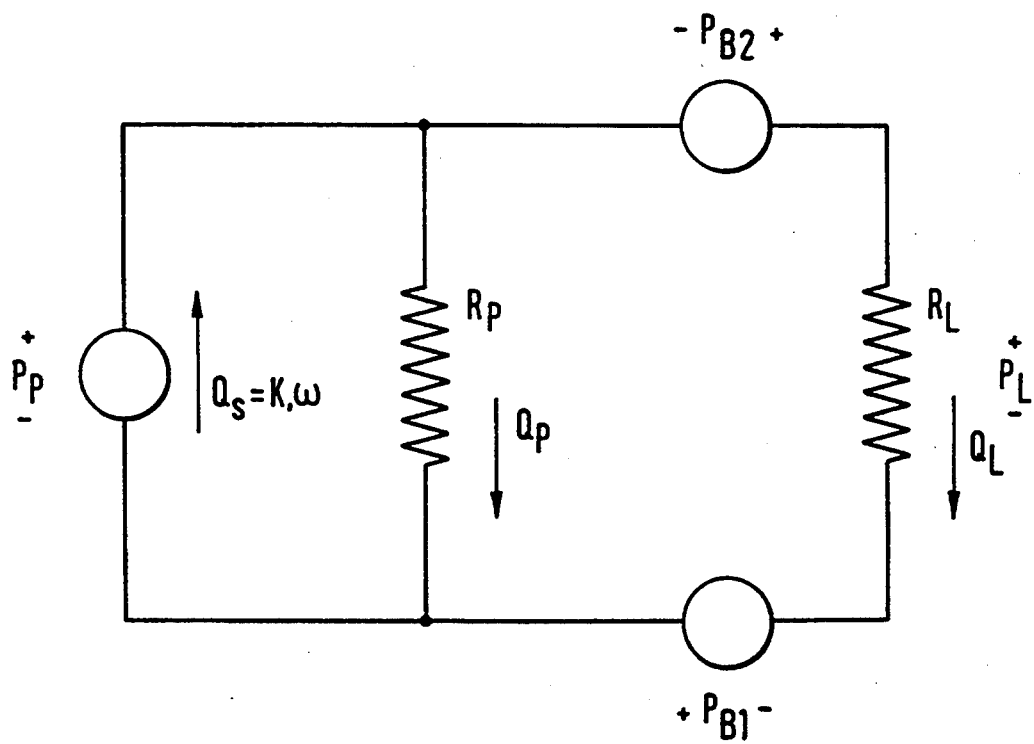
FIG. 3 is a hydraulic circuit model related to the preferred embodiments.

FIG. 3 is a hydraulic circuit model for the gear pump 20 and it's load, wherein:

$Q_S$ = source flow rate of gear pump
$Q_P$ = backflow in pump
$Q_L$ = flow in load
$\omega$ = rotation rate of gear pump
$K_1$ = a constant equal to the volume of fluid displaced by the gear teeth per revolution of the pump
$R_P$ = hydraulic resistance of the pump backflow leakage path
$R_L$ = hydraulic resistance of the load on the pump
$P_P$ = pressure drop across the pump
$P_L$ = pressure drop across the load Discussion of pressure sources $P_{B1}$ and $P_{B2}$ will be deferred for the present and for this discussion will be assumed to have a value of zero and thus have no effect. $Q_S$ is the flow source which results from the volume of fluid between the gear teeth being displaced from the inlet of the pump to the outlet by the rotation of the gears. The flow rate is directly proportional to the rotation rate of the gears with the relationship of:

$$Q_S(\text{mL/min}) = K_1(\text{mL/rev}) \cdot \omega(\text{rev/min})$$

Figure 5:
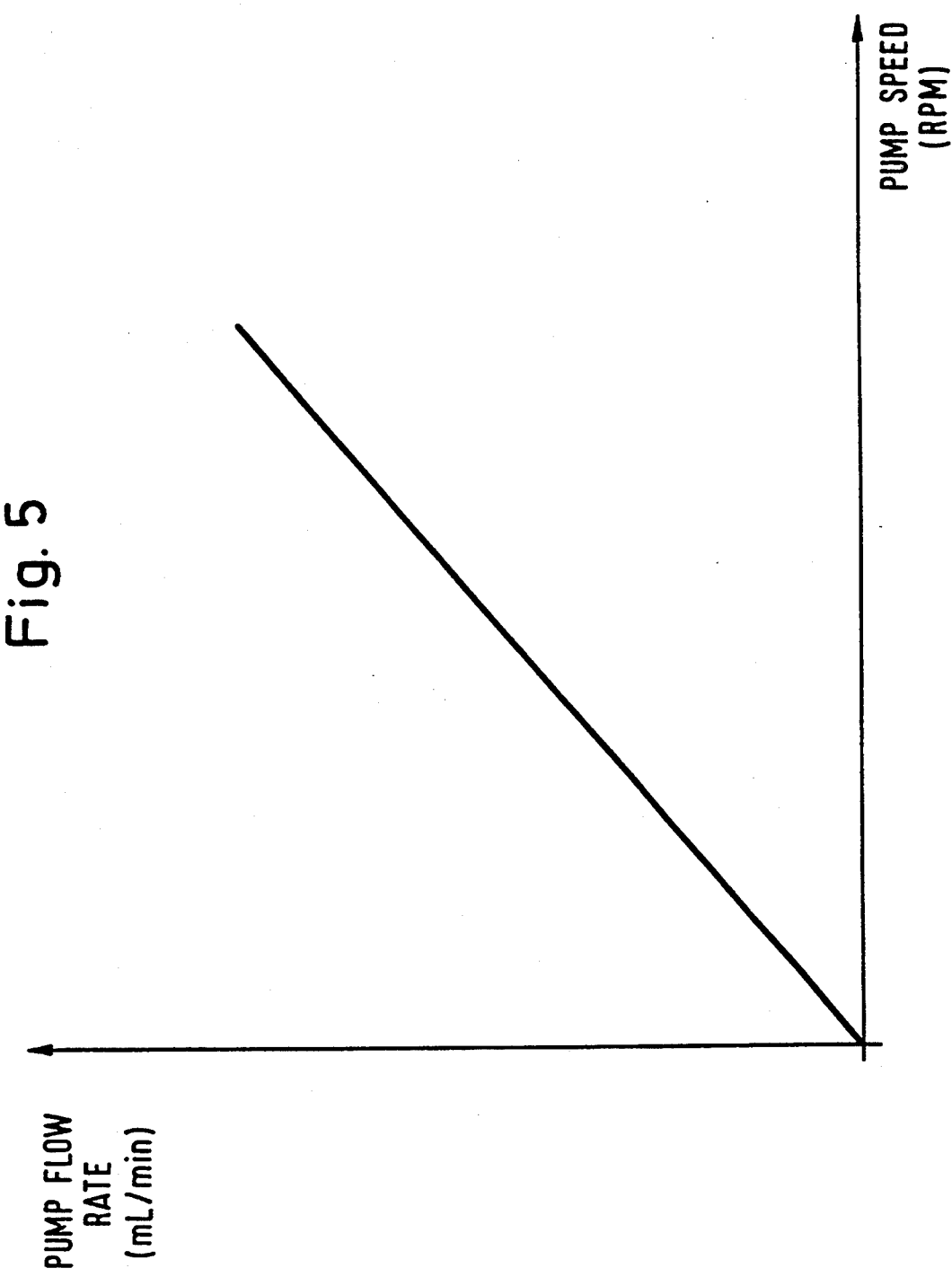
FIG. 5 is a graph of flow versus pump speed for a typical gear pump at zero differential pressure.

This direct linear relationship is illustrated in FIG. 5. The pressure $P_P$ appears across the flow source $Q_S$ and the backflow resistance $R_P$. The pressure $P_L$ appears across the load resistance $R_L$. The pressure $P_P$ will produce a flow in the pump backflow resistance of $Q_P$ and the pressure $P_L$ will produce a flow in the load of $Q_L$. The relationship of flow, resistance, and pressure (i.e., the hydraulic equivalent of Ohm's law) is:

$$P_P = Q_P \cdot R_P$$

$$P_L = Q_L \cdot R_L$$

It can be seen that the following relationship (i.e., the hydraulic equivalent to Kirchoff's laws in electrical circuits) applies:

$$Q_S = Q_P + Q_L$$

$$P_P = P_L = P$$

Therefore:

$$\begin{aligned} Q_L &= Q_S - Q_P \\ &= (K_1 \cdot \omega) - (P/R_P) \end{aligned}$$

This model is the basis of the flow control systems useful in embodiments of the present invention. P is measured by the pressure transducer 21, $\omega$ is measured by the tachometer 20-6, and $K_1$ is a known constant from the manufactured dimensions of the gear pump 20.

Figure 6:
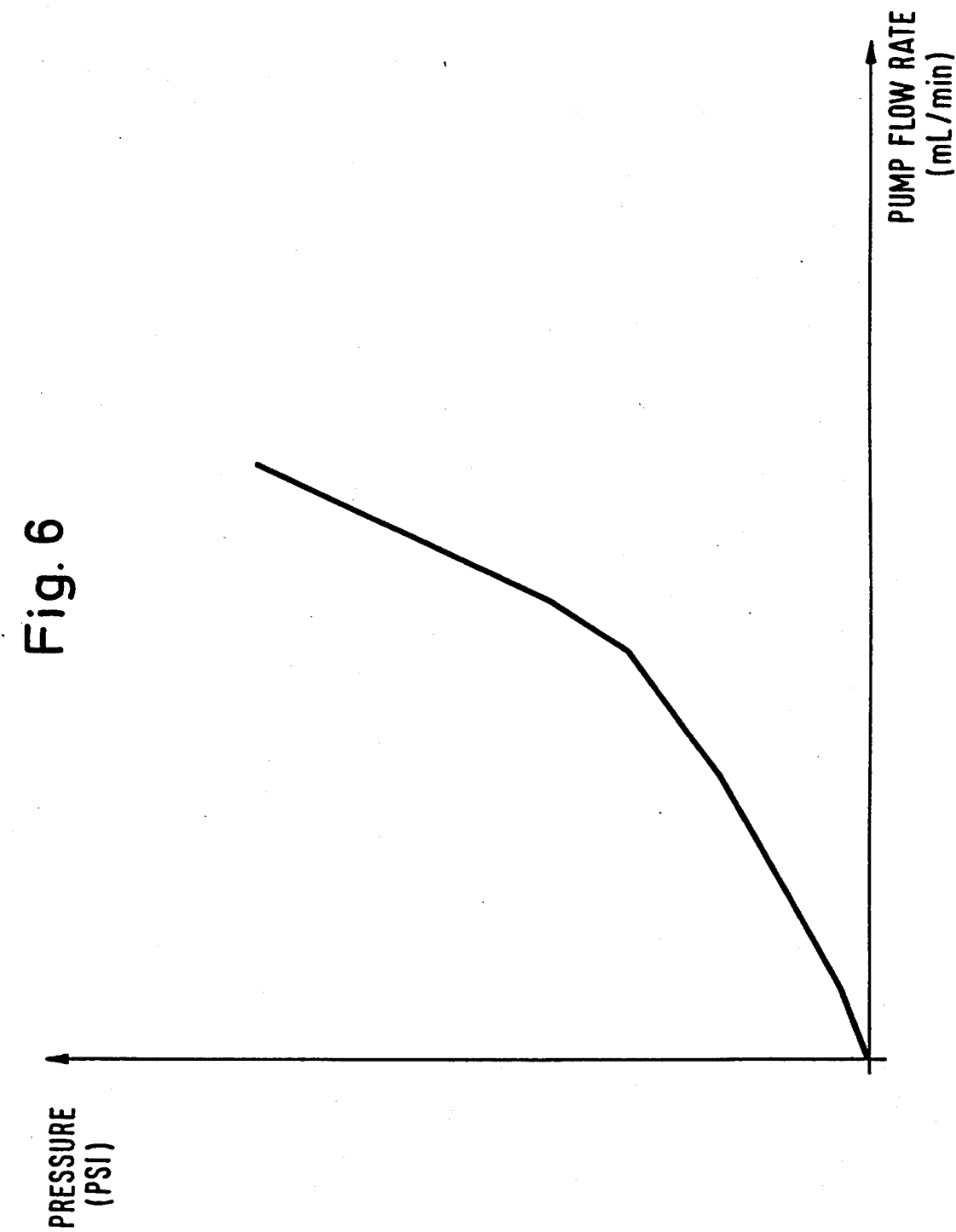
FIG. 6 is a graph of pressure versus flow for the backflow hydraulic resistance in a typical gear pump.
Figure 7:
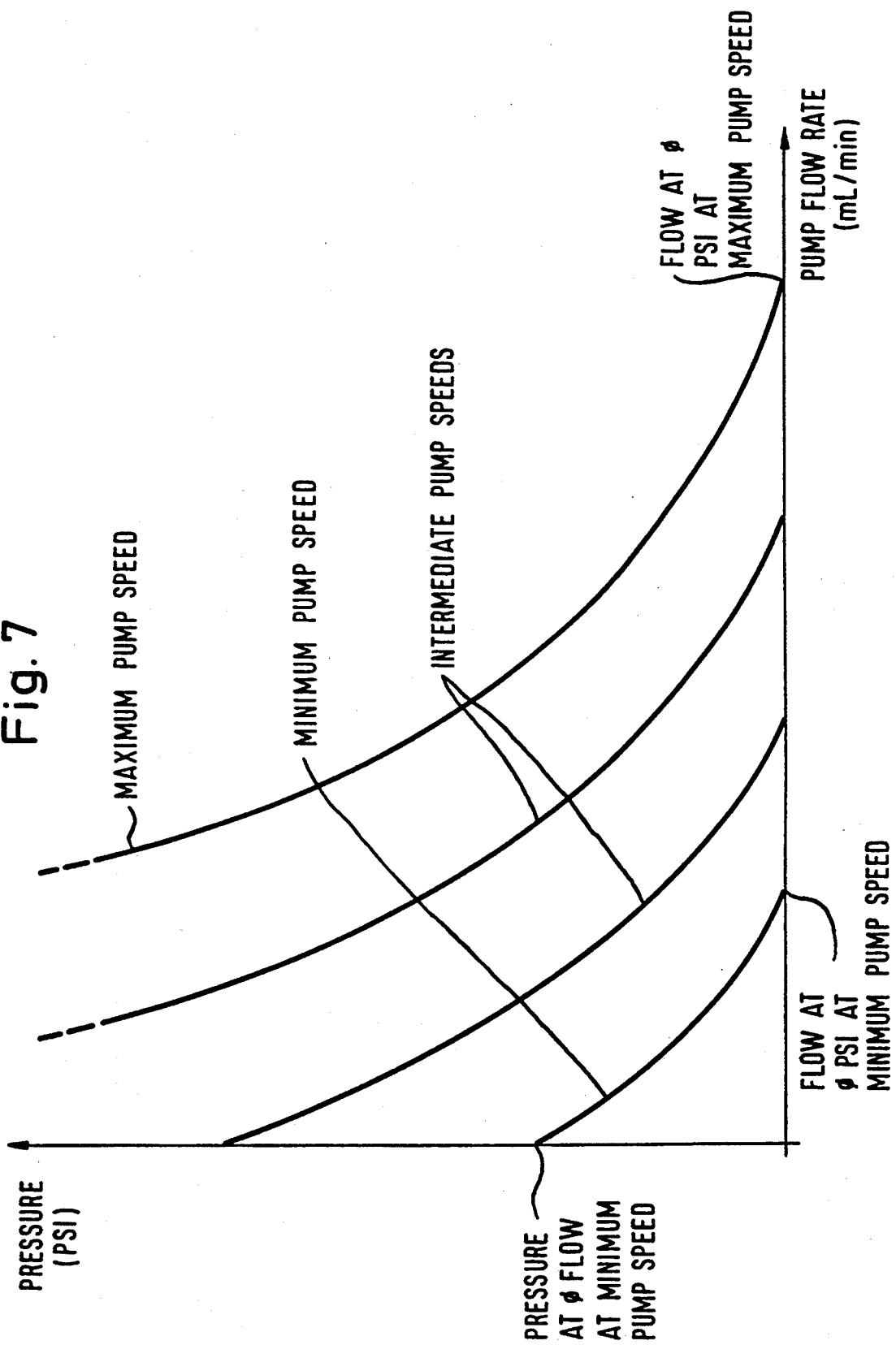
FIG. 7 is a family of graphs of pressure versus flow delivered to a load for a typical gear pump operated at a variety of speeds.

The flow versus pressure characteristics of the backflow resistance $R_P$ can be affected by numerous mechanical and hydraulic effects and is in general not a linear relationship. This non-linear relationship is generically illustrated in FIG. 6. The increase of resistance with flow is typical in certain embodiments, but is not a requirement of the invention as any non-linear relationship can be accommodated. The flow versus pressure in the load resistance may be either linear or non-linear depending upon the characteristics of the separation device 24 utilized in the system 10.

Figure 8:
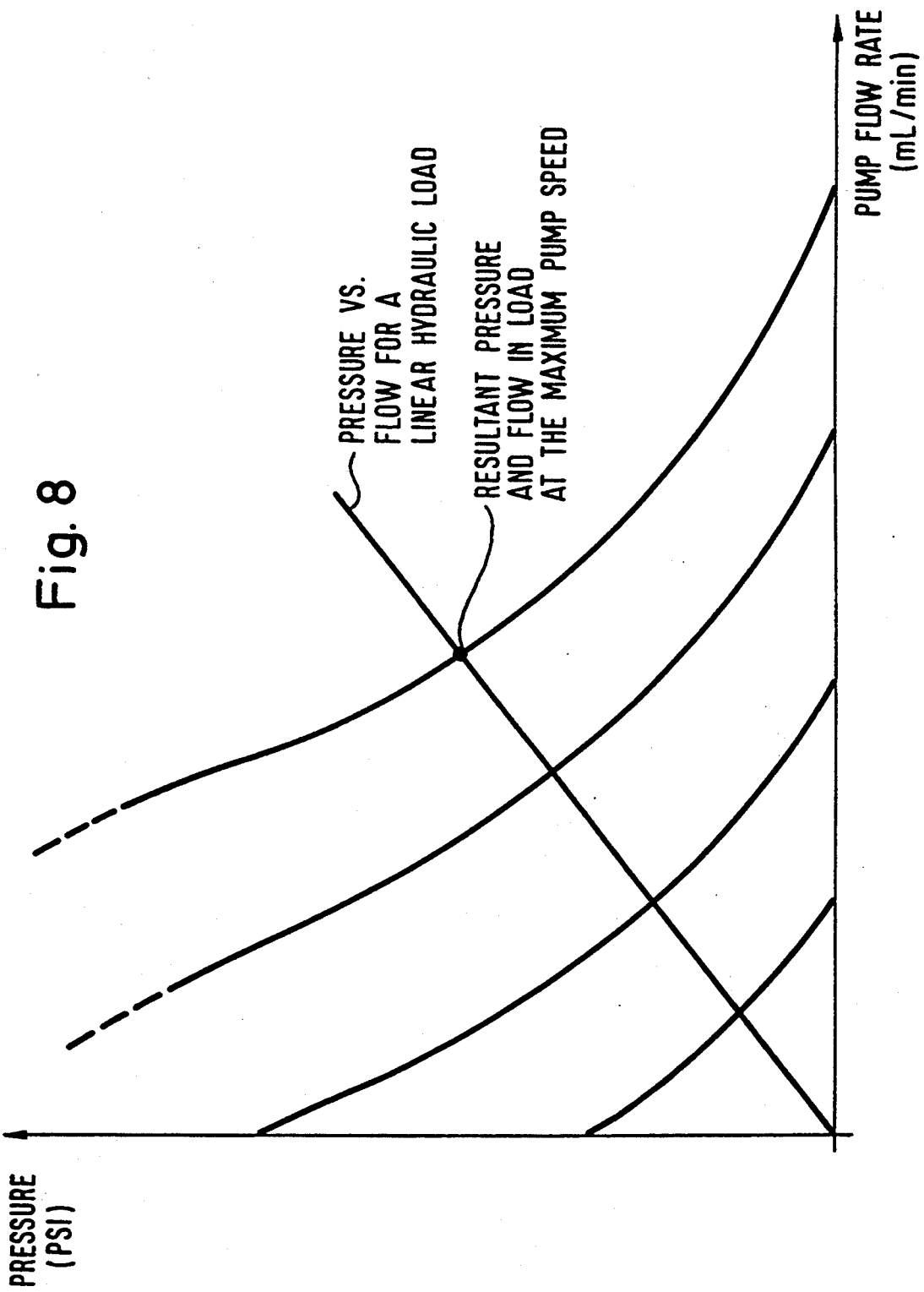
FIG. 8 is the graph of FIG. 7 with a linear hydraulic load superimposed upon it.
Figure 9:
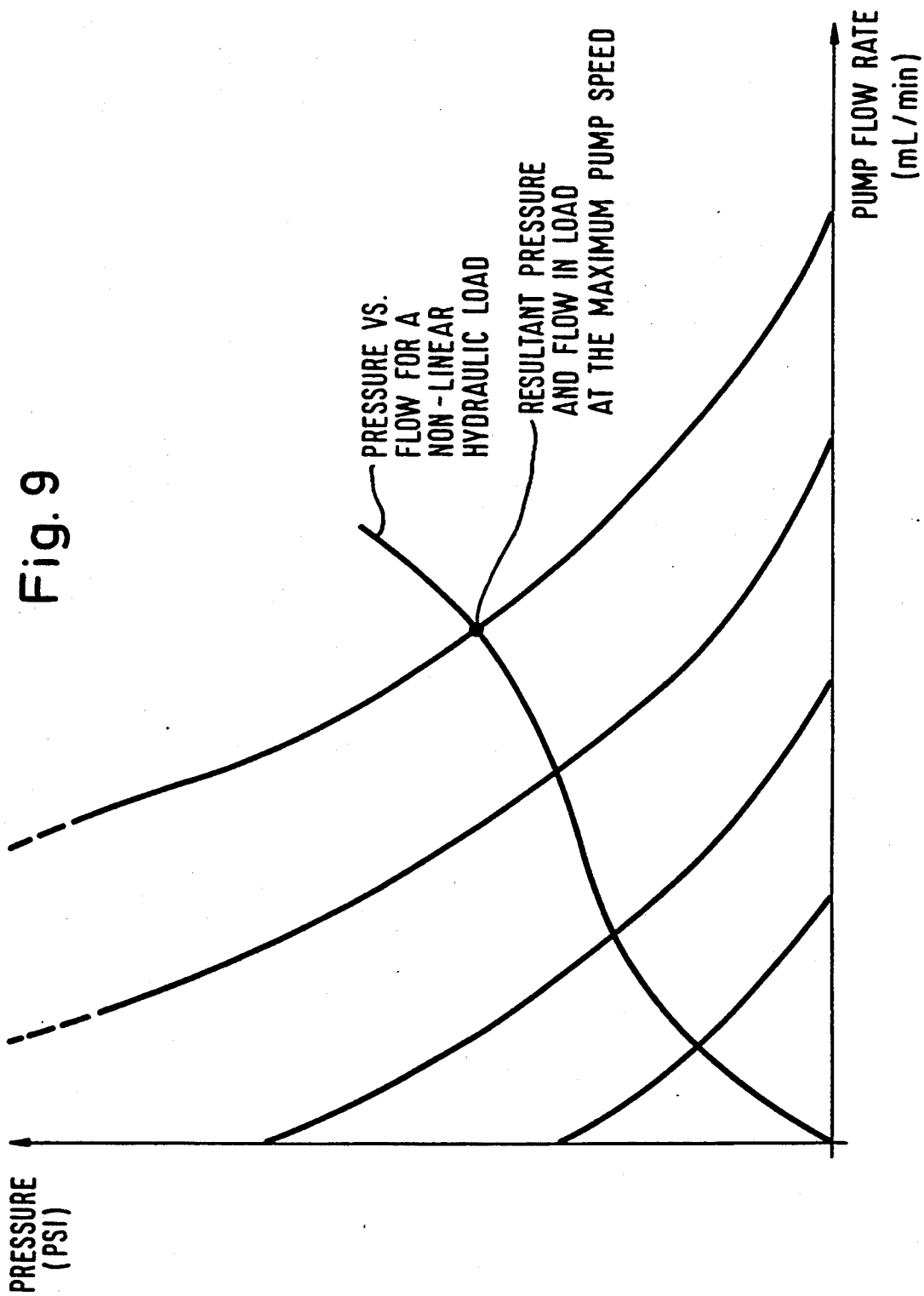
FIG. 9 is the graph of FIG. 7 with a non-linear hydraulic load superimposed upon it.

By combining the information presented in FIGS. 3, 5 and 6, FIG. 7 is produced which illustrates the relationship of pump speed, pressure, and flow in the load. Each curve in the family results from computing the source flow $Q_S$ for a given pump speed from FIG. 5, using that as the flow at zero pressure, and subtracting the graph of FIG. 6 from that point as this graph represents the flow lost to the backflow versus pressure. By superimposing the flow versus pressure characteristics of a load on this family of curves, the operating pressure and flow of the system may be determined. FIG. 8 illustrates a linear load thus superimposed and FIG. 9 similarly illustrates a non-linear load.

Figure 4:
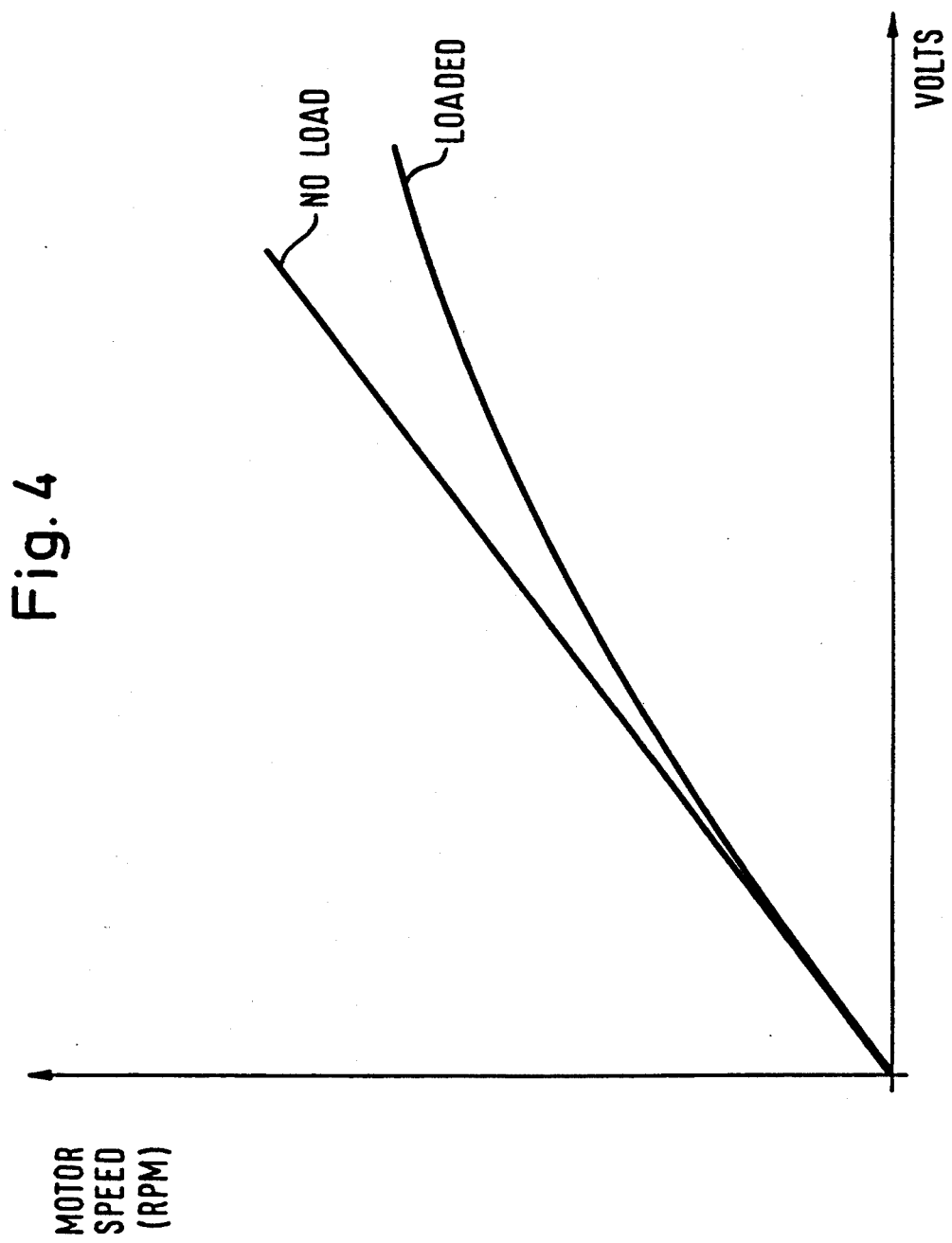
FIG. 4 is a graph of motor speed versus applied voltage for various motor loads for a motor usable in the preferred embodiments.

In a preferred embodiment, a parameter which is driven by the controller 30 is the voltage to the DC motor 20-5 which in turn drives the pump 20. The typical relationships between the applied voltage and the motor speed is illustrated in FIG. 4. Since this relationship is dependent on the load on the pump, the pump speed is determined by direct measurement with the tachometer 20-6. A synchronous motor could be used in place of the motor-tachometer combination of this embodiment.

In one preferred flow control method, a linear load resistance is required. The controller 30 works in concert with an operator to measure the resistance of the load by servoing the pump to a fixed pressure, timing the delivery of flow, and receiving operator entry of the volume delivered. The resistance is then computed from:

$$R_L = (\text{pressure})/(\text{volume/time})$$

This resistance is displayed to the operator and may be re-entered by the operator at a later time or used at that time. To set a flow in a linear load of known resistance, the controller computes the required pressure from:

$$P_L = Q_L \cdot R_L$$

and servos to that pressure. This method is of particular utility with high resistance loads where a large percentage of the source flow $Q_S$ flows through the backflow path in the pump.

In a second preferred flow control method, linearity is not required provided that the ratio of flow in the pump backflow to the flow in the load does not become too large. The controller 30 works in concert with the operator to measure the backflow pressure versus flow characteristics of the individual pump by having the operator plug the outlet of the pump (equivalent to making $R_L$ infinite), operating the pump at a sequence of speeds, measuring and storing pressure and speed (and thus $Q_S$). By examining FIG. 3, it can be seen that when $R_L$ is infinite, $Q_S$ equals $Q_P$. By measuring and storing values of $Q_P$ versus P, the controller can compute $Q_P$ from a measured P at a later time. To compute the flow in an unknown load, the controller measures the pump speed $\omega$ from the tachometer and source flow $Q_S$ from:

$$Q_S = K_1 \cdot \omega$$

and then subtracts the computed flow in the backflow $Q_P$. A preferred computation method for $Q_P$ is linear interpolation between discrete stored $Q_P$, P pairs. Once thus calibrated, this flow computation method can operate on a variety of loads and needs no further calibration unless the backflow characteristics of the pump change. To set a flow in an unknown load, the controller servos the computed flow to the desired value.

In a preferred embodiment, composition control is accomplished in a manner similar to that taught by Carson in U.S. Pat. No. 4,595,496. The percentage of the total composition which is represented by each of the fluids contained in reservoirs 12, 13, 14 and 15 is determined by the percentage of time which the respective valves 16, 17, 18 and 19 are open out of the total time for a complete cycling of these valves. Gradients (the variation of composition in time in a predetermined fashion) are produced by the controller 30 by changing the relative timing of the four valves within each total valve cycle time in a manner determined by a stored, operator entered program. Undesired fluctuations resulting from intermodulation (heterodyning) of pump frequencies and valve cycle time frequencies are minimized by maintaining certain fixed ratios between these frequencies as taught by Carson. These ratios are such that energy in the beat frequencies which pass through a subsequent filter (mixer) are minimized. Multiple ratios are stored in the controller, each associated with a range of pump speeds. The controller selects a ratio appropriate to a pump speed and then uses that ratio to compute the valve cycle time from the pump speed as measured by the tachometer 20-6. This preferred embodiment differs from the embodiment described in Carson in that the pump fundamental frequency is always greater than that of the valve cycle rather than less, that the speed of the pump is measured rather than directly set by the controller, and that a gear pump has less flow fluctuation at the higher harmonics of the pump fundamental frequency than do typical dual piston pumps.

Due to their interactive nature, there is dependency among the control schemes. The order of dependency of the various control systems executed in this embodiment are:

1. The flow is determined by that set in a stored control program entered by the operator.
2. The pump speed is set by the controller in order to produce that flow.
3. The total valve cycle time is determined by the controller from the pump speed.
4. The individual valve times and hence the resultant fluid composition are determined by the controller from an operator entered, stored control program.

The fluid composition at the common outlet point of the aforementioned valves is a flowing sequence of small segments of the individual fluids contained in the respective reservoirs. In order that the composition be that of the average of the composition of these segments, the small segments must be effectively mixed. If them is too little mixing, them will be a residual fluctuation in composition at the valve cycle frequency. If there is too much mixing, the rate of change of composition of the system will be unnecessarily limited. Mixing is accomplished in this preferred embodiment in the cylindrical chamber formed between the gear pump drive magnet and the chamber which encloses and seals the magnet. The narrow spacing between the stationary wall and the rotating magnet forms a region of high shear in the fluid which acts as an effective mixer. This mixer has a very low unswept volume (i.e., a region occupied by the fluid in the system with a significantly lower flow through it than the remainder of the volume) which is advantageous in producing rapid and accurate changes in composition. The compactness of the integrated pump and mixer is advantageous in reducing the delay volume (i.e., the volume between the point of formation of composition and the separation device) which also contributes to a rapid composition response. An important characteristic of mixing in this system is to have a sharp frequency cut off (the equivalent of a multi-pole falter in electrical terms) which will have a high degree of attenuation of undesired fluctuations in composition while still allowing a rapid change in composition when desirable. An active, powered, high shear mixer such as utilized in this embodiment is effective at accomplishing this.

The injector 22 in this preferred embodiment is a septum (not shown) between the flowing fluid and the external environment located just prior to the separation device 24. A sample is injected using a needle and syringe into the system for separation. The low maximum pressures of this embodiment allow the use of this form of injection. Other forms of injection as practiced in the art could also be used to advantage.

Any separation device whose working pressure and flow characteristics are appropriate to this embodiment may be used to advantage. Membrane based separation devices are of particular interest as they take significant advantage of the high flow, rapid composition response, low composition fluctuation characteristics of the embodiment, and themselves produce low back pressures.

The detector 26 in this embodiment is an ultraviolet absorbance measurement through a flow cell (not shown) as has been commonly practiced in the chromatography art. The output signal of the detector is made externally available for further processing. Any detector appropriate to the samples being separated could be used to advantage.

The stream of fluid containing the separated components of the sample are delivered to external apparatus such as fraction collectors which physically separate the segments of fluid containing the separated components.

Referring again to FIG. 3, the pressure sources $P_{B1}$ and $P_{B2}$ will now be described. If the pressure $P_P$ across the gear pump backflow resistance $R_P$ can be reduced to zero, then the flow through the backflow resistance $Q_P$ will also be reduced to zero and the flow in the load $Q_L$ becomes equal to $Q_S$ (again applying the equivalent of Kirchoffs laws). This situation occurs when:

$$P_{B1}+P_{B2}=P_L \text{ or}$$

$$P_{B1}+P_{B2}=Q_L \cdot R_L \text{ or}$$

$$P_{B1}+P_{B2}=Q_S \cdot R_L$$

This means that if one or both of the pressure sources $P_{B1}$ and $P_{B2}$ can be controlled such that the pressure across the pump $P_P$ is zero, then How control becomes simply:

$$Q_S=Q_L=K_1 \cdot \omega$$

This condition is unique in that flow is produced by one pump and pressure is produced by another thereby allowing the characteristics of each pump to be tailored to that function without requiring a single pump to perform both functions. The following two alternate embodiments illustrate the application of this principle in practical systems.

Figure 10:
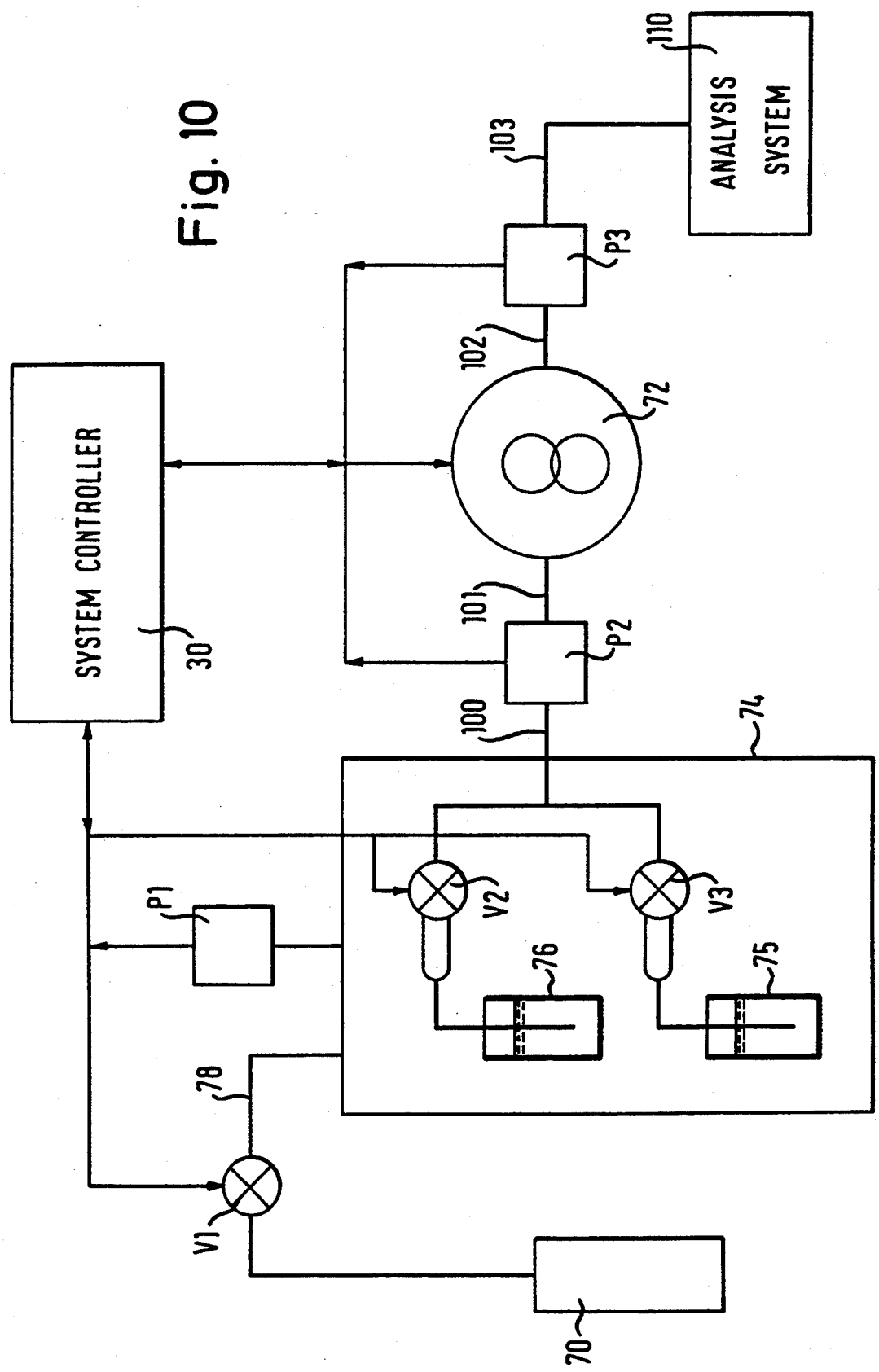
FIG. 10 is a schematic block diagram of a high pressure LC system according to a preferred embodiment of the invention.

FIG. 10 shows a first alternate embodiment with a high pressure pump metering system using a gear pump as a metering pump. For a user selected flow rate the system controller 30 activates the previously characterized gear pump 72. The system controller monitors the pressure on each side of the pump via transducers P2 and P3. A pressurized chamber 74 holds two containers of fluid 75 and 76 each with a feed tube positioned in the fluid. The pressure in the chamber is monitored by the controller via the pressure transducer P1. A pressurized tube 78 pressurizes the chamber with the tube feed through a vented valve V1 from a pressure source 70. This pressurized chamber corresponds to pressure source $P_{B1}$ in FIG. 3. The pressurizing gas is selected to substantially not become dissolved into the fluids and/or to diffuse out of the fluid through the walls of robes 100, 101, 102 and 103 prior to reaching the analysis system 110. The system controller sets the pump speed to correspond to the desired pump flow rate and also substantially maintains a zero pressure differential across the pump by adjusting the pressure in the chamber 74 by controlling valve V1. Under these conditions the gear pump acts as a positive displacement pump with the delivered flow substantially equal to the flow produced by the gear tooth displacement. In this embodiment the pump is able to run at the high pressures (up to several thousand psi) found in many HPLC analytic systems.

Figure 11:
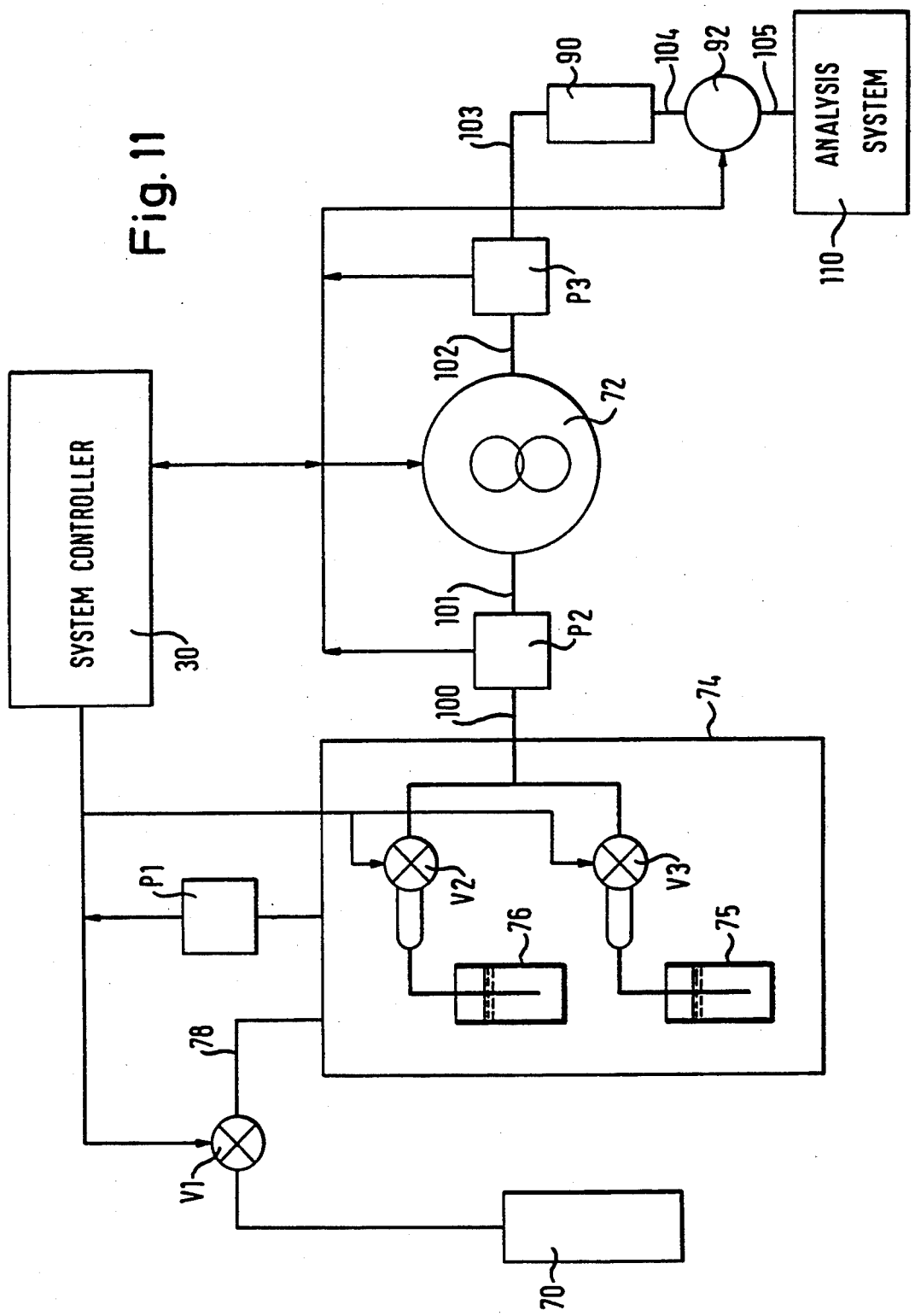
FIG. 11 is a schematic block diagram of a second high pressure LC system according to a preferred embodiment of the invention.

FIG. 11 shows a second alternate embodiment wherein a gear pump can be used as a metering pump in high pressure applications. In this embodiment, which is similarly configured to the embodiment of FIG. 10 (and where like components have the same reference designations), the output of the gear pump 72 operates at atmospheric pressure. Alternatively, if desired, the gear pump output pressure may be elevated above atmospheric pressure. In that case the chamber to pressurize containers 75, 76 (corresponding to pressure source $P_{B1}$ in FIG. 3) in a manner similar to that discussed with respect to the FIG. 10 embodiment is required. The output of the gear pump 72 is fed to a booster pump 92 (corresponding to pressure source $P_{B2}$ in FIG. 3) to elevate the pressure to significantly higher system operating pressures (e.g. up to 5000 p.s.i.). Interposed between the gear pump and the booster pump may be an accumulator 90 to compensate for intake flow pulsation's of the booster pump. The system controller 70 adjusts the speed of the booster pump via readings from transducer P3 to drive the outlet pressure of the gear pump (P3) to be substantially equal to its inlet pressure (P2) i.e., controlled to maintain zero differential pressure across the gear pump. Alternatively, the booster pump may be of the type which can accept varying flow rates from the gear pump while holding its intake pressure essentially constant.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. A magnetically coupled gear pump having plural gears for producing fluid flow from an inlet liquid stream of non-uniform composition comprising:
   a) a magnetic rotor, magnetically coupled to a driving magnetic means located external to the path of said fluid flow, said rotor adapted for rotational movement when activated and having a stationary bearing shaft on which rotates at least one gear of said gear pump, whereby said rotor drives said gears;
   b) said flow path being configured such that said liquid stream enters said chamber to an outlet port to create an exit flow path for liquid exiting from said gear pump through said interior passageway such that all parts of the volume in said chamber surrounding said magnetic rotor are flushed uniformly thereby producing a rapid washout of the entire pump volume when the average composition of said inlet liquid stream is changed.

2. The apparatus of claim 1 further comprising means to control the flow rate of said gear pump.

* * * * *